US009951115B2

(12) United States Patent
Soares (10) Patent No.: US 9,951,115 B2
(45) Date of Patent: *Apr. 24, 2018

(54) CGRP AGONIST PEPTIDES (71) Applicant: Christopher J. Soares, La Jolla, CA (US)

(72) Inventor: Christopher J. Soares, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/908,515

(22) PCT Filed: Jul. 29, 2014

(86) PCT No.: PCT/US2014/048724
§ 371 (c)(1),
(2) Date: Jan. 28, 2016

(87) PCT Pub. No.: WO2015/017455
PCT Pub. Date: Feb. 5, 2015

(65) Prior Publication Data
US 2016/0207975 A1 Jul. 21, 2016

Related U.S. Application Data (60) Provisional application No. 61/860,244, filed on Jul. 30, 2013.

(51) Int. Cl.
*C07K 14/575* (2006.01)
*A61K 38/00* (2006.01)

(52) U.S. Cl.
CPC ........ *C07K 14/57527* (2013.01); *A61K 38/00* (2013.01)

(58) Field of Classification Search
CPC .................. C07K 14/57527; A61K 38/225
See application file for complete search history.

(56) References Cited

U.S. PATENT DOCUMENTS 9,193,776 B2 * 11/2015 Soares ............. C07K 14/57527
2008/0274952 A1 * 11/2008 Soares ................. C07K 14/575
514/4.8

FOREIGN PATENT DOCUMENTS

| EP | 2 127 676 A2 | 12/2009 |
| WO | WO 94/21665 * | 9/1994 |
| WO | WO 2006/083254 A1 | 8/2006 |
| WO | WO 2006/105345 | 10/2006 |
| WO | WO 2007/055743 A2 | 5/2007 |
| WO | WO 2009/064298 A1 | 6/2009 |
| WO | WO 2010/107874 A2 | 9/2010 |
| WO | WO 2013/059336 A1 | 4/2013 |
| WO | WO 2013/112912 A1 | 8/2013 |

OTHER PUBLICATIONS

Database Geneseq, "Amylin agonist peptide, SEQ:114.", XP002732365, retrieved from EBI accession No. GSP:AYJ13652 Database accession No. AYJ13652 sequence No. 114., Nov. 11, 2010.
Database Geneseq, "Amylin agonist peptide, SEQ:106.", XP002732366, retrieved from EBI accession No. GSP:AYJ13644 Database accession No. AYJ13644 sequence ID No. 106., Nov. 11, 2010.
Banerjee, Sugato, et al., "Identification of specific calcitonin-like receptor residues important for calcitonin gene-related peptide high affinity binding," *BMC Pharmacology*, vol. 6, No. 9, Jun. 15, 2006, pp. 1-12.
Heino Paivi, "Binding of CGRP Analogs and their Effect on Adenylate Cyclase Activity in Porcine Iris-Ciliary Body," *Journal of Ocular Pharmacology and Therapeutics*, vol. 14, No. 6, Dec. 1998, pp. 543-554.
Lehninger, *Principles of Biochemistry*, fourth edition, Freeman and Company, 2005, pp. 120-122.
Schellenberger, Volker, et al., "A recombinant polypeptide extends the in vivo half-life of peptides and proteins in a tunable manner," *Nature Biotechnology*, vol. 27, No. 12, Dec. 1, 2009, pp. 1186-1190.
Watkins, et al., "Structure-activity relationships for α-calcitonin gene-related peptide," *British Journal of Pharmacology*, 170, pp. 1308-1322, 2013.
International Search Report and Written Opinion received in PCT/US2014/048724, dated Nov. 28, 2014.
Communication dated Mar. 3, 2017 in the European Application 14752510.9 filed Feb. 24, 2016.

* cited by examiner

*Primary Examiner* — Christina Bradley
(74) *Attorney, Agent, or Firm* — Knobbe Martens Olson & Bear LLP (57) ABSTRACT

The embodiments provide a calcitonin gene-related peptide (CGRP) agonist peptide or pharmaceutically acceptable salt thereof, including pharmaceutical compositions comprising a CGRP agonist peptide. The embodiments further provide treatment methods, including method of treating metabolic disorders and metabolic disorders selected from metabolic syndrome, diabetes and obesity. The methods involve administering to a subject in need thereof an effective amount of CGRP peptide.

13 Claims, 6 Drawing Sheets

Figure 6

CGRP AGONIST PEPTIDES

CROSS REFERENCE TO RELATED APPLICATIONS

This application is a U.S. National Phase Application of PCT International Application Number PCT/US2014/048724, filed on. Jul. 29, 2014, designating the United States of America and published in the English language. This application further claims priority to U.S. Provisional Patent Application 61/860,244 filed on Jul. 30, 2013 and entitled "CGRP AGONIST PEPTIDES." The disclosures of the above-referenced applications are hereby expressly incorporated by reference in their entirety.

REFERENCE TO SEQUENCE LISTING

The present application is being filed along with a sequence listing in Electronic format. The Sequence Listing is provided as a file entitled CSOAR.002W0 SECOND REVISION.TXT, created Jan. 5, 2016, which is approximately 8 kb in size. The information in the electronic format of the sequence listing is incorporated herein by reference in its entirety in its entirety.

BACKGROUND OF THE INVENTION

Field of the Invention

The present invention relates to peptide agonists of the calcitonin/calcitonin gene-related peptide (CT/CGRP) family of peptide hormones and therapeutic uses thereof.

Description of the Related Art

The CT/CGRP peptide family includes calcitonin gene-related peptide (CGRP), adrenomedullin (ADM), intermedin (IM), calcitonin (CT) and amylin. The biological actions of these peptides are mediated via binding to two closely related type II G protein-coupled receptors, the calcitonin receptor (CTR) and the calcitonin receptor-like receptor (CRLR) (Christopoulos, et al. 1999, *Mol. Pharmacol.* 56:235-242; Poyner et al. 2002 *Pharmacol. Rev.* 54:233-246). Although the calcitonin receptor is the main mediator for calcitonin action, it preferentially binds amylin, when the receptor is associated with a receptor activity modifying protein (RAMP) (see, e.g., Tilikaratne, et al. 2000, *J. Pharmacol, Exp. Ther.* 294(1):61-72). Cloning and functional studies have shown that CGRP, ADM, IM and, to a lesser extent, amylin likewise interact with different combinations of CRLR and the three receptor activity modifying proteins (RAMP-1, RAMP-2 and RAMP-3); see, e.g., McLatchie et al. 1998, *Nature* 393:333-339 and Roh et al. 2004, *JBC* 279(8):7264-7274), In fact, co-expression of the calcitonin receptor-like receptor (CRLR) and receptor activity-modifying proteins (RAMPs) is required to generate functional receptors for calcitonin gene-related peptide (CGRP), adrenomedullin (ADM) and intermedin (IM). The formation of heterodimers between RAMPs and CRLR is essential for the proper cell surface targeting and pharmacological characteristics of CGRP, ADM and IM receptors. Co-expression of RAMP-1 with CRLR leads to the formation of a CGRP receptor, whereas RAMP-2 and RAMP-3 co-expression with CRLR form ADM and IM receptors respectively (Miret, et al. 2002, *JBC* 277(9):6881-6887.) IM has been shown to be a nonselective agonist for all three RAMP/CRLR co-receptors.

The physiological functions of the hormone peptides in the CT/CGRP family are determined by receptor-binding specificity and the tissue expression profiles of individual ligands and their respective receptors and have been shown to be involved in cardiovascular morphogenesis, sensory neurotransmission, inflammatory reactions, nociceptive behavior and glucose homeostasis (see, e.g., Hay, et al. 2001, *Trends Pharmacol, Sci,* 22:57-59; Shindo, et al. 2001, *Circulation* 104:1964-1971; Zhang et al. 2001, *Pain* 89:265-273; Salmon et al. (1999) *Neuroreport* 10:849-854; Salmon, et al. 2001, *Nat. Neurosci.* 4: 357-358; and Mulder, et al. 2000, Am. J. Physiol. 278:E684-E691).

Calcitonin gene-related peptide (CGRP) is a peptide which, in several species, exists in two forms, designated CGRP-alpha and CGRP-beta (or CGRP-1 and CGRP-11, respectively). CGRP peptides are highly conserved across species, for example, human and rat CGRP-alpha peptides share 89% amino acid homology (the mature peptides differing by four amino acids) compared to 92% amino acid homology between human alpha- and beta-CGRP (which differ by 3 amino acids). (See for example, Ma, H. 2004, *Nature and Science* 2(3):41-47.) A well-studied peptide in the CT/CGRP family of peptide hormones, CGRP is a 37 amino acid vasoactive neuropeptide that is released from sensory, motor and enteric nerves comprising an amphiphilic α-helical secondary structure in the amino acid sequence between residues 8-25. CGRP has potent vasodilatory and cardiotonic action, as described, for example, in U.S. Pat. No. 4,530,838 to Evans, et al. CGRP is present in both the central and peripheral nervous systems and is concentrated in those areas of the body receiving sensory input from the dorsal horn with limited amounts associated with autonomic input. In the brain, the peptide is present in the nuclei of sensory and motor cranial nerves and in cell bodies in the hypothalamus, preoptic area, ventromedial thalamus, hippocampus, and the like (Poyner, D. 1992, *Pharmac. Ther.* 56:23-51).

CGRP is known to be involved in various pharmacological effects, such as: 1) vasodilation, 2) muscle and liver AMP kinase (AMPK) activation and lipolysis and/or fat oxidation, 3) reduction in food intake, 4) inhibition of gastric emptying and modification of gut function and 5) increased glycolysis and inhibition of glycogen synthesis. The net physiological significance of these effects is not completely understood; however, evidence of CGRP's role in fatty acid oxidation and regulation of lipid availability and utilization has been demonstrated (Danaher, et al. 2008 Endocrinology 149(1): 154-160). Studies have demonstrated CGRP's role in inhibition of food intake including evidence that its action is via the paraventricular nucleus (PVN) of the hypothalamus. (See for example, Martinez-Alvarez, R M, et al. 2009 *Peptides* 30(4):803-807 and Dhillo, W. S, et al. 2002, *Endocrine Abstracts* 3OC43; ISSN1470-3947.) Additionally, it has been shown that CGRP stimulate GLP-1 secretion, a protein known to play an important role in amelioration of diabetes.

Metabolic syndrome is a disease state manifested by obesity, insulin resistance, dyslipidemia and hypertension. Today, these four manifestations are treated by selective treatment paradigms. Native CGRP has a half-life of less than 30 minutes, and a short duration of pharmacological actions after CGRP infusions is evident. Due to vasodilatory effects of administered CGRP, in vivo pharmacological studies of native CGRP can be difficult due to the secondary effects of vasodilation and compensatory vasoconstrictive actions. Thus, the pharmacological usefulness of CGRP, particularly with respect to long-term or chronic use thereof, requires the generation of CGRP analogues with prolonged action and some effects may even only be obtained with longer-acting analogues. Similarly, to be viable as a therapeutic agent, particularly for chronic use, analogues having prolonged action are desirable.

SUMMARY OF THE INVENTION

In one aspect, the present invention provides calcitonin gene-related peptide (CGRP) agonists comprising the structure of Formula I:

$$X^1\text{—}Y^1\text{—}Z^1 \qquad (I)$$

wherein:

$X^1$ is an N-terminal fragment comprising at least about five to about seven amino acid residues having the general formula:

$X_1\ X_2\ X_3\ \text{Thr}\ X_4\ \text{Thr}\ \text{Cys}$ (SEQ ID NO: 6)

wherein $X_1$ is Ala or Cys or is not present, $X_2$ is Cys, Ser or Gly, provided however that at least one of $X_1$ and $X_2$ is Cys and only one of $X_1$ or $X_2$ is Cys, $X_3$ is Asp or Asn and $X_4$ is Ala or Ser and wherein the terminal Cys of $X^1$ is capable of forming a disulfide bridge with the Cys residue in $X_1$ or $X_2$;

$Y^1$ is a central core comprising at least about 12 to about 24 and preferably about 15 amino acid residues wherein at least some of the residues of the central core are capable of forming an α-helix under physiological conditions, said central core having the general formula:

$X_5\ \text{Lys}\ \text{Leu}\ \text{Gly}\ \text{Arg}\ X_6\ X_7\ \text{Gln}\ X_8\ X_9\ X_{10}\ \text{Arg}\ X_{11}\ X_{12}\ \text{Thr}\ X_{13}$ (SEQ ID NO: 7)

wherein $X_5$ is Val or Met, $X_6$ is Leu or Tyr, $X_7$ is Ser or Thr, $X_8$ is Asp or Glu, $X_9$ is Phe or Leu, $X_{10}$ is His or Asn, $X_{11}$ is Phe or Lys, $X_{12}$ is His or Gln, $X_{13}$ is Phe or Tyr;

and $Z^1$ is a C-terminal fragment comprising at least about six to about twelve amino acid residues, preferably about ten amino acid residues, said C-terminal fragment comprising a C-terminal amide, said fragment having the general formula:

Pro $X_{14}$ Thr $X_{15}$ Val Gly Ser Lys Ala Phe (SEQ ID NO: 8), wherein $X_{14}$ is Arg or Gln and $X_{15}$ is Asn or Ala;

or pharmaceutically acceptable salt thereof, wherein said CGRP agonist has a higher binding affinity for human CGRP receptor than does human CGRP.

In some embodiments, $X^1$ comprises 6 or 7 amino acids. In some embodiments, $Y^1$ comprises 15 amino acids. In some embodiments, $Z^1$ comprises 10 amino acids. In some embodiments, $X^1$ comprises 6 or 7 amino acids, $Y^1$ comprises 15 amino acids and $Z^1$ comprises 10 amino acids.

In some embodiments, $X_1$ is Cys, and $X_2$ is Ser or Gly. In some embodiments, $X_2$ is Cys, and $X_1$ is Ala. In some embodiments, $X^1$ comprises SEQ ID NO: 9. In some embodiments, $Z^1$ comprises SEQ ID NO: 10.

In some embodiments, a calcitonin gene-related peptide (CGRP) agonist is provided. In some embodiments, the calcitonin gene-related peptide (CGRP) agonist selected from the group comprising SEQ ID NO:1, SEQ ID NO:2, SEQ ID NO:3, SEQ ID NO:4 and SEQ ID NO:5 or a pharmaceutically acceptable salt thereof. In some embodiments, the calcitonin gene-related peptide (CGRP) agonist comprises at least 90% sequence identity to the amino acid sequence of SEQ ID NO:1, SEQ ID NO:2, SEQ ID NO:3, SEQ ID NO:4 and SEQ ID NO:5 or a pharmaceutically acceptable salt thereof. In some embodiments, the calcitonin gene-related peptide (CGRP) agonist comprises at least 80% sequence identity to the amino acid sequence of SEQ ID NO:1, SEQ ID NO:2, SEQ ID NO:3, SEQ ID NO:4 and SEQ ID NO:5 or a pharmaceutically acceptable salt thereof.

In some embodiments, the calcitonin gene-related peptide (CGRP) agonist comprises an N-terminal addition of an XTENS polypeptide. In some embodiments, the calcitonin gene-related peptide (CGRP) agonist comprises an amino terminus modified with a derivative group. In some embodiments, the derivative group is selected from acetyl, aryl, aralkyl, acyl, epoxysuccinyl and cholesteryl groups.

In some embodiments, the calcitonin gene-related peptide (CGRP) agonist comprises a carboxy-terminus modified with a derivative group. In some embodiments, the derivative group is selected from alcohol, aldehyde, epoxysuccinate, acid halide, carbonyl, halomethane, diazomethane groups and carboxamide. In some embodiments, the calcitonin gene-related peptide (CGRP) agonist comprises a C-terminal carboxy group replaced by an amide group. In some embodiments, the amide group comprises the structure —C(O)NH$_2$.

In some embodiments, a pharmaceutical composition comprising a calcitonin gene-related peptide (CGRP) agonist of the present invention is provided. In some embodiments, the pharmaceutical composition comprises an acceptable excipient and any of the embodiments described above.

In some embodiments, a method of treating a metabolic disorder is provided. In some embodiments, the method comprises administering to a subject in need thereof an effective amount of the calcitonin gene-related peptide (CGRP) agonist of the present invention. In some embodiments, the subject is human.

In some embodiments, a method of treating a metabolic disorder selected from the group comprising metabolic syndrome, diabetes and obesity is provided. In some embodiments, the method comprises administering to a subject in need thereof an effective amount of the calcitonin gene-related peptide (CGRP) agonist. In some embodiments, the subject is human.

In some embodiments, a method of increasing glycolysis in a subject is provided. In some embodiments, the method comprises administering an effective amount of the calcitonin gene-related peptide (CGRP) agonist of the present invention. In some embodiments, a method of increasing AMPK, activation in a subject is provided. In some embodiments, the method comprises administering an effective amount of the calcitonin gene-related peptide (CGRP) agonist of the present invention.

In some embodiments, the subject is suffering from insulin resistance. In some embodiments, the subject is suffering from type-2 diabetes mellitus. In some embodiments, the subject is suffering from hypertension. In some embodiments, the subject is suffering from dyslipidaemia. In some embodiments, the subject is suffering from atherosclerosis. In some embodiments, the subject is suffering from thrombosis.

DETAILED DESCRIPTION OF THE PREFERRED EMBODIMENT

In one aspect, the present invention provides calcitonin gene-related peptide agonist having the structure of Formula I:

$$X^1—Y^1—Z^1 \quad (I)$$

wherein:

$X^1$ is an N-terminal fragment comprising at least about five to about seven amino acid residues having the general formula:

(SEQ ID NO: 6)
$X_1$ $X_2$ $X_3$ Thr $X_4$ Thr Cys wherein $X_1$ is Ala or Cys or is not present, $X_2$ is Cys, Ser or Gly, provided however that at least one of $X_1$ and $X_2$ is Cys and only one of $X_1$ or $X_2$ is Cys, $X_3$ is Asp or Asn and $X_4$ is Ala or Ser and wherein the terminal Cys of $X^1$ is capable of forming a disulfide bridge with the Cys residue in $X_1$ or $X_2$;

$Y^1$ is a central core comprising at least about 12 to about 24 and preferably about 15 amino acid residues wherein at least some of the residues of the central core are capable of forming an α-helix under physiological conditions, said central core having the general formula:

(SEQ ID NO: 7)
$X_5$ Leu Gly Arg $X_6$ $X_7$ Gln $X_8$ $X_9$ $X_{10}$ Arg $X_{11}$ $X_{12}$ Thr $X_{13}$ wherein $X_5$ is Val or Met, $X_6$ is Leu or Tyr, $X_7$ is Ser or Thr, $X_8$ is Asp or Glu, $X_9$ is Phe or Leu, $X_{10}$ is His or Asn, $X_{11}$ is Phe or Leu, $X_{12}$ is His or Gln, $X_{13}$ is Phe or Tyr; and $Z^1$ is a C-terminal fragment comprising at least about six to about twelve amino acid residues, preferably about ten amino acid residues, said C-terminal fragment comprising a C-terminal amide, said fragment having the general formula:

(SEQ ID NO: 8)
Pro $X_{14}$ Thr $X_{15}$ Val Gly Ser Lys Ala Phe, wherein $X_{14}$ is Arg or Gln and $X_{15}$ is Asn or Ala;
or pharmaceutically acceptable salt thereof, wherein said CGRP agonist has a higher binding affinity for human CGRP receptor than does human CGRP.

In some embodiments, $X^1$ comprises the sequence, SEQ ID NO: 9 (ACDTATC).

In some embodiments, $Z^1$ comprises the sequence, SEQ ID NO: 10 (PRTNVGSKAF).

Some CGRP agonists, according to the present invention, comprise: an amino acid sequence having at least 80%, preferably 90%, sequence identity to the amino acid sequence of SEQ ID NOS: 1, 2, 3, 4 or 5 wherein said peptide retains agonist activity.

Some embodiments provide a pharmaceutical composition comprising a pharmaceutically acceptable excipient and a calcitonin gene-related peptide agonist as disclosed and described herein.

Some embodiments provide a method of treating a condition associated with insufficient levels of CGRP or that are ameliorated by increased CGRP said method comprising the administration of a calcitonin gene-related peptide agonist as disclosed and described herein, to an individual, the method comprising administering to the individual an effective amount of a calcitonin gene-related peptide agonist as disclosed and described herein.

Some embodiments provide a calcitonin gene-related peptide agonist having the structure selected from the following peptide sequences, listed in Table 1.

TABLE 1

| | |
|---|---|
| NH$_2$-ACDTATCVLGRLSQELHRLQTYPRTNVGSKAF-NH$_2$; | (SEQ ID NO: 1)-NH$_2$ |
| NH$_2$-ACDTATCVLGRLSQELHRLQTYPTNVGSKAF-NH$_2$; | (SEQ ID NO: 2)-NH$_2$ |
| NH$_2$-CDTATCVLGRLSQELHRLQTYPRTNVGSKAF-NH$_2$; | (SEQ ID NO: 3)-NH$_2$ |
| NH$_2$-CDTATCVLGRLSQELHRLQTYPTNVGSKAF-NH$_2$; | (SEQ ID NO: 4)-NH$_2$ |
| NH$_2$-ACDTATCMLGRYTQDFNRFHTFPRTNVGSKAF-NH$_2$; | (SEQ ID NO: 5)-NH$_2$ |

In some embodiments, the amino acid sequence of the calcitonin gene-related peptide agonist can be modified, relative to the sequence of SEQ ID NOS: 1, 2, 3, 4 or 5 such that the modification reduces the calcitonin gene-related peptide agonist's susceptibility to enzymatic proteolysis. In some embodiments this modification may comprise the N-terminal addition of a sequence comprising all or part of the 864 residue XTENS polypeptide, a polypeptide that has been shown to increase protein stability after administration to a subject. See, for example, Schellenberger, et al., 2009, *Nature Biotechnology* 27(12): 1186-1192, which is hereby incorporated by reference in its entirely.

DEFINITIONS

As used herein, "agonist" refers to a biologically active ligand which binds to its complementary biologically active receptor and activates the latter either to cause a biological response in the receptor or to enhance preexisting biological activity of the receptor.

As used herein, "C-terminal amide" refers to an amide moiety which replaces the C-terminal hydroxyl moiety usually present at the carboxy-terminus of a polypeptide, such that the polypeptide ends with a carboxamide (i.e., C(=O)—NH2) rather than a C-terminal carboxy (i.e. C(=O)—OH) moiety. For a description of pharmaceutically acceptable amides as prodrugs, see Bundgaard, H. ed. 1985 *Design of Prodrugs* Elsevier Science Publishers, Amsterdam. These amides are typically formed from the corresponding carboxylic acid and an amine. Generality, amide formation can be accomplished via conventional synthetic techniques. See, for example, March, 1992 *Advanced Organic Chemistry*, 4th Ed., John Wiley & Sons, New York, p. 393 and Mark, et al. 1980 *Encyclopedia of Chemical Technology*, John Wiley & Sons, New York.

As used herein, the term "α-helix" means a structural component that forms an α-helical protein structure or any other structural analogue which results in a similar positioning of the $X^1$ and $Z^1$ domains on a receptor.

As used herein, "pharmaceutically acceptable carrier" refers to a carrier medium which does not interfere with the effectiveness of the biological activity of the active ingredients and which is not toxic to the host or patient.

As used herein, "pharmaceutically acceptable salt" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the modified calcitonin gene-related peptide agonists disclosed herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Thus, the term refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable salts as prodrugs, see Bundgaard, H. ed., 1985 *Design of Prodrugs*, Elsevier Science Publishers, Amsterdam.

As used herein, "therapeutically- or pharmaceutically-effective amount" as applied to the compositions as disclosed herein refers to the amount of composition sufficient to induce a desired biological result. That result can be alleviation of the signs, symptoms, or causes of a disease, or any other desired alteration of a biological system.

The amino- and/or carboxy-terminus of the peptide compounds disclosed herein can be unmodified hydrogen. Alternatively, the amino- and/or carboxy-terminus of the peptide compound can be modified with a derivative group. Amino-derivative groups which can be present at the N-terminus of a peptide compound include acetyl, aryl, aralkyl, acyl, epoxysuccinyl and cholesteryl groups. Carboxy-derivative groups which can be present at the C-terminus of a peptide compound include alcohol, aldehyde, epoxysuccinate, acid halide, carbonyl, halomethane, diazomethane groups and carboxamide. In preferred embodiments, the amino terminus is unmodified hydrogen and the carboxy-terminus is modified with a carboxamide derivative group.

One-letter abbreviations for the canonical amino acids and three-letter abbreviations (in parentheses) are provided in Table 2:

TABLE 2

| | |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |
| Lysine (Lys) | K |
| Threonine (Thr) | T |
| Asparagine (Asn) | N |
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

Nomenclature and Symbolism for Amino Acids and Peptides by the UPAC-IUB Joint Commission on Biochemical Nomenclature (JCBN) have been published in the following documents: *Biochem. J.*, 1984, 219, 345-373; *Eur. J. Biochem.*, 1984, 138, 9-5 37; 1985, 152, 1; 1993, 213, 2; *Internat. J. Pept. Prot. Res.*, 1984, 24, following p 84; *J. Biol. Chem.*, 1985, 260, 14-42; *Pure Appl. Chem.*, 1984, 56, 595-624; *Amino Acids and Peptides*, 1985, 16, 387-410; *Biochemical Nomenclature and Related Documents*, $2^{nd}$ edition, Portland Press, 1992, pages 39-69.

Amino acids are sometimes referred to herein by the usual three letter codes and/or one letter codes. If, due to typing errors, there are deviations from the commonly used codes, the commonly used codes apply.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ClustalW2, Kalign, MAFFT, or Megalign (DNAS-TAR) software. Those skilled in the art can determine appropriate parameters for measuring alignment, including any algorithms needed to achieve maximal alignment over the full length of the sequences being compared.

PREPARATION OF PEPTIDES

Solid Phase Synthesis

The calcitonin gene-related peptide agonists described herein can be prepared by classical methods known in the art, for example, by using standard solid phase techniques. See, for example, Merrifield, 1963 *J. Am. Chem. Soc.* 85:2149, incorporated herein by reference in their entirety. These solid phase peptide synthesis procedures are well known in the art and further described by J. M. Stewart and J. D. Young, 1984 *Solid Phase Peptide Syntheses* 2nd Ed., Pierce Chemical Company and by M. Bodanszky, 1993, *Principles of Peptide Synthesis*, 2$^{nd}$ Ed., Springer Laboratory.

C-Terminal Modifications

CGRP agonists of the present invention preferably comprise a C-terminal amide, wherein the C-terminal carboxyl group is replaced by an amide —C(O)NR$^3$R$^4$, wherein R$^3$ and R$^4$ are preferably hydrogen (H) but may either or both be a functional group selected, for example, to protect the C-terminal amide from enzymatic degradation and/or to prolong the half-life of the peptide compound in vivo, provided however such functional groups do not interfere with, or are modified or removed in vivo to permit, binding of the peptide compound to the CGRP receptor. Such functional groups are well known to those of skill in the art; see for example, Kahns, A. and Bundgaard, H. 1991 *Pharmaceutical Research* 8(12):1533-1538. Techniques for synthesis of such C-terminal amides are also well known to those of skill in the art.

In some embodiments, the calcitonin gene-related peptide agonists as disclosed and described herein may also be prepared by recombinant DNA techniques well known in the art. Such recombinantly produced CGRP peptide agonists may be further modified, for example to replace the C-terminal carboxyl group with an amide, after recombinant production using techniques well known in the art, including for example, enzymatic conversion of the acid to the amide.

Pharmacological Formulations

The compositions containing the CORP peptide agonists of the present invention can be administered for prophylactic and/or therapeutic treatments. In therapeutic applications, compositions are administered to a patient already suffering from a disease, as described above, in an amount sufficient to cure or at least partially arrest or ameliorate the symptoms of the disease and/or its complications. An amount adequate to accomplish this is defined as a "therapeutically effective amount" or "therapeutically effective dose". Amounts effective for this use will depend, for example, on the severity of the disease and the weight and general state of the patient, and can be readily determined by one of ordinary skill in the art.

In prophylactic applications, compositions containing the compounds disclosed herein are administered to a patient susceptible to or otherwise at risk of a particular disease and are sufficient to prevent, delay or lessen the severity of the disease. Such an amount is defined to be a "prophylactically effective amount" or "prophylactically effective dose." In this use, the precise amounts again depend, for example, on the patient's state of health and weight, and can be readily determined by one of ordinary skill in the art.

In some embodiments, a therapeutically effective amount of a compound of the present invention is administered to a subject (for example, patient or animal) suffering from insulin resistance, type-2 diabetes mellitus, hypertension, obesity, dyslipidaemia, atherosclerosis and/or thrombosis. The dosage ranges for the administration of a compound of this invention are those large enough to produce a therapeutic effect.

Some embodiments include pharmaceutical compositions comprising, as an active ingredient, at least one of the peptides disclosed herein in association with a pharmaceutical carrier or diluent. These pharmaceutical compositions can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, intranasal or sublingual routes of administration and can be formulated in dosage forms appropriate for each route of administration. See, for example, Bernstein, et al. PCT Patent Publication No, WO 93/25221, published Dec. 23, 1993; Pitt, et al. PCT Patent Publication No. WO 94/17784, published Aug. 18, 1994; and Pitt, et al. European Patent Application 613,683, published Sep. 7, 1994, each of which is incorporated herein by reference in its entirety.

Suitable routes of administration are likewise known to those of skill in the art and may include, for example and without limitation, oral, transmucosai or topical; parenteral delivery, including intramuscular, subcutaneous, intravenous, intramedullary injections, intrathecal, intraperitoneal, intranasal, or intraocular injections, as well as needle-free subcutaneous delivery. The compounds can also be administered in sustained or controlled release dosage forms, including without limitation, depot injections, osmotic pumps, transdermal (including electrotransport) patches, and the like, for prolonged and/or timed, pulsed administration at a predetermined rate.

The pharmaceutical compositions of the present embodiments may be manufactured in a manner that is itself known, e.g., by means of conventional dissolving, granulating, dragee-making, levigating, emulsifying, encapsulating, entrapping or tabletting processes.

Pharmaceutical compositions for use in accordance with the present embodiments thus may be formulated in conventional manner using one or more physiologically acceptable carriers comprising excipients and auxiliaries which facilitate processing of the active compounds into preparations which can be used pharmaceutically and which are appropriate for the intended route of administration. Any of the well-known techniques, carriers, and excipients may be used as suitable and as understood in the art; e.g., in Remington's Pharmaceutical Sciences, above.

Although the exact dosage will be determined on a drug-by-drug and disease-by-disease basis, in most cases, some generalizations regarding the dosage can be made, and those of skill in the pharmacology art will understand from the disclosure herein that appropriate doses can be determined using routine techniques. Usually the doses for a compound of this invention would fall in a concentration of from about $10^{-15}$ M to $10^{-5}$ M (for example, as measured in one or more of muscle, blood, serum or plasma).

The amount of a compound of this invention administered to an animal to achieve a desired level or concentration of the compound of this invention will depend on a number of factors well known to practitioners, such as compound half-life (for example, serum half-life), and the frequency and mode of administration. For illustration and not limitation, the dose of a compound of the present invention may be administered in the range from 20 picograms to 1 gram, more often between 3 nanograms and 500 micrograms per dose. In various embodiments, the unit dosage (in some cases daily dosage) is less than about 100 micrograms, less than about 10 micrograms, less than about 1 microgram, less than about 100 nanograms, less than about 10 nanograms, less than about 1 nanogram, less than about 100 picograms, or less than about 10 picograms.

Other ranges of a compound of this invention will be apparent to the skilled practitioner based on data from initial dose-response curves and other data that can be obtained by routine methods. In cases of administration of a pharmaceutically acceptable salt, dosages may be calculated as the free base. In some embodiments, the composition is administered 1 to 4 times per day or as a single acute dose. In some embodiments, the peptides will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

A compound of the present invention can be formulated or co-administered with other active agents that, for example, also treat metabolic or cardiovascular diseases/disorders.

Throughout the specification, any recitation of a particular compound should be understood to encompass that compound and any (other) pharmaceutically acceptable salts thereof.

Other Utility

The compounds described herein are useful in vitro as unique tools for understanding the biological role of CGRP. The present compounds are also useful in the development of other compounds that bind to and activate CGRP receptors, because the present compounds provide important information on the relationship between structure and activity to facilitate such development.

EXAMPLES

The following examples are provided to further illustrate the instant embodiments. They are not meant to limit the scope of the embodiments.

Example 1

Cell-based GPCR Profiling Assays. A representative CGRP agonist peptide according to the present invention, ACX017 (SEQ ID NO:1), was profiled against G-Protein Coupled Receptors (GPCRs) in cell-based assays to determine its agonist activity and dose response. Results of the CGRP and adrenomedullin receptor screens are provided below. Assays were performed using the SelectScreen® Cell-based GPCR Profiling Services by Life Technologies, Carlsbad, Calif.

CALCRL:RAMP1 CRE-bla Freestyle 293F—Agonist Screen (CGRP Receptor)

CALCRL:RAMP1-CRE-bla Freestyle 293F cells were thawed and resuspended in Assay Media (DMEM, 10% dialyzed FBS, 25 mM HEPES pH 7.3, 0.1 mM NEAA, 100 U/mL/100 µg/mL Pen/Strep) to a concentration of 312,500 cells/mL. 32 µL of cell suspension (10,000 cells) was added to each well of a 384-well Poly-D-Lysine assay plate. Cells in Assay Media were incubated for 16-24 hours in the plate at 37° C./5% CO2 in a humidified incubator. 4 µL of a 10× serial dilution of CGRP or ACX017 was added to appropriate wells of the plate. 4 µL of Assay Media was added to all wells to bring the final assay volume to 40 µL. The plate was incubated for 5 hours at 37° C./5% CO2 in a humidified incubator, 8 µL of 1 µM Substrate+Solution D Loading Solution was added to each well and the plate was incubated for 2 hours at room temperature. The plate was read on a fluorescence plate reader.

CALCRL:RAMP3—CRE-bla Freestyle 293F—Agonist Screen (Adrenomedullin 2 Receptor)

CALCRL:RAMP3-CRE-bla Freestyle 293F cells were thawed and resuspended in Assay Media (DMEM, 10% dialyzed FBS, 25 mM HEPES pH 7.3, 0.1 mM NEAA, 100 U/mL/100 µg/mL Pen/Strep) to a concentration of 312,500 cells/mL. 32 µL of cell suspension (10,000 cells) was added to each well of a 384-well Poly-D-Lysine assay plate. Cells in Assay Media were incubated for 16-24 hours in the plate at 37° C./5% CO2 in a humidified incubator. 4 µL of a 10× serial dilution of Adrenomedullin or ACX017 were added to appropriate wells of the plate. 4 µL of Assay Media was added to all wells to bring the final assay volume to 40 µL. The plate was incubated for 5 hours at 37° C./5% CO2 in a humidified incubator. 8 µl of 1 µM Substrate+Solution D Loading Solution was added to each well and the plate was incubated for 2 hours at room temperature. The plate was read on a fluorescence plate reader.

The following controls were run on each plate for each individual cell line:

Full Agonist control. The full agonist control contained 0.1% DMSO, cells and a maximum concentration of the known agonist. The full agonist control was used to determine the upper end of the assay or 100% activation.

No Agonist control. The no agonist control contained 0.1% DMSO, cells and assay media in place of the agonist. The no against control was used to determine the lower end of the assay or 0% activation.

Cell-free Control. The cell-free control contained 0.1% DMSO and assay media. It was used to determine the background fluorescence for both coumarin and fluorescein wavelengths. This value was used for background subtraction.

Known Agonist. A known agonist titration was run on every plate for each cell-line to ensure the cell line was activated within an expected EC50/IC50 range as previously determined.

Figure 1:
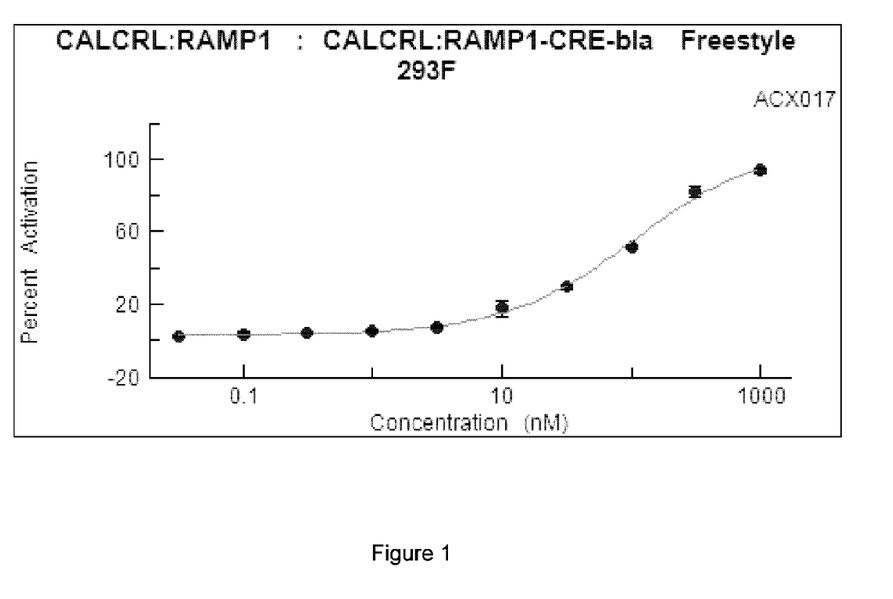
FIG. 1 provides results of the CALCRL:RAMP1—CRE-bla Freestyle 293F agonist screen described in Example 1 below. The graph of concentration of ACX017 (SEQ ID NO: 1) versus percent activation of the CGRP receptor demonstrates that a CGRP agonist of the present invention activated the CGRP receptor with an EC50 concentration of about 105 nM.
Figure 2:
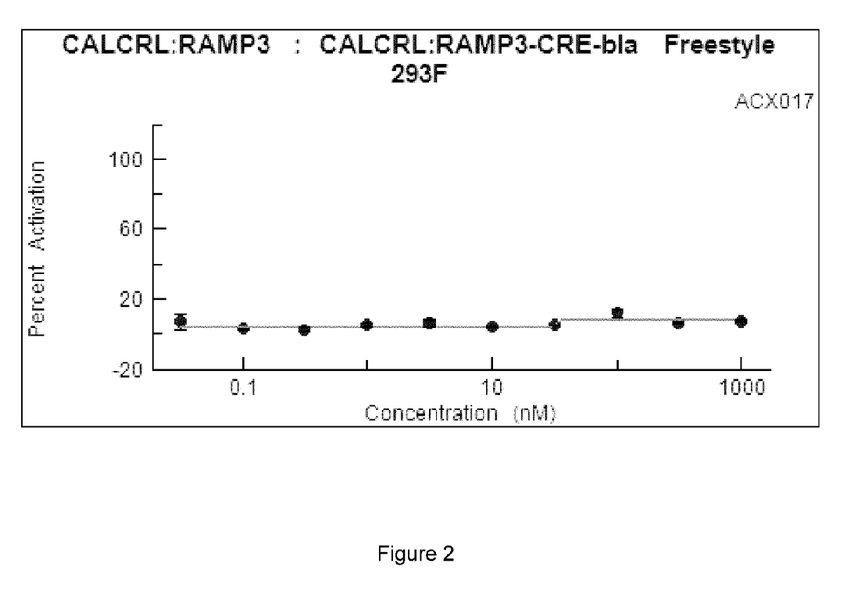
FIG. 2 provides results of the CALCRL:RAMP3—CRE-bla Freestyle 293F agonist screen described in Example 1 below. The graph of concentration of ACX017 (SEQ ID NO: 1) versus percent activation of the adrenomedullin 2 (AM2) receptor demonstrates that a CGRP agonist of the present invention did not activate the adrenomedullin 2 (AM2) receptor.
Figure 3:
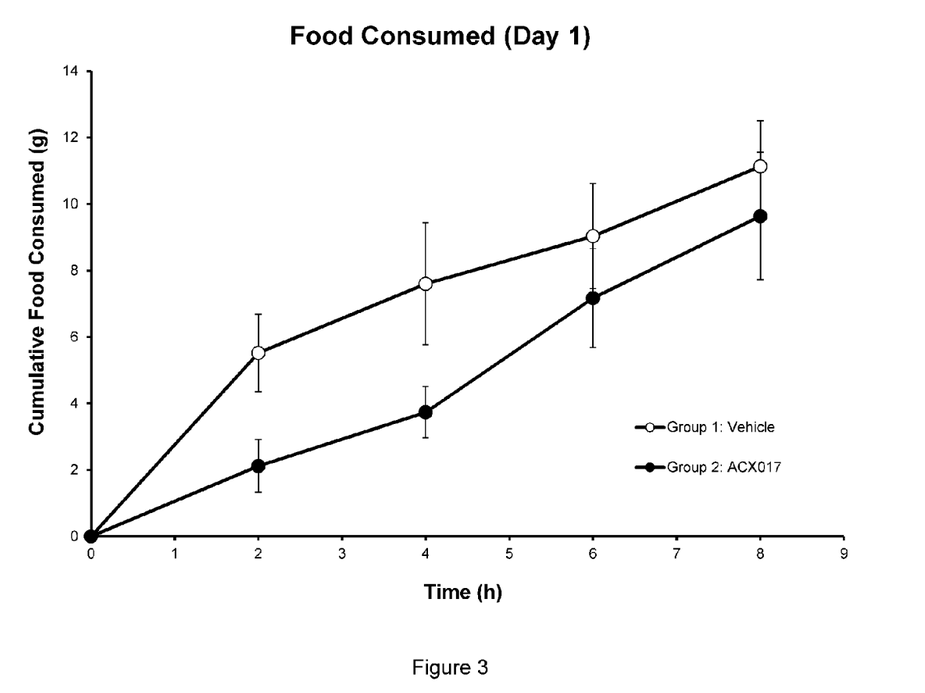
FIGS. 3-6 provide results of the four-day food intake study, described in Example 2 herein. The effect on cumulative food intake for each of Days 1-4 are shown in FIGS. 3-6, respectively. Graphed is cumulative food intake of each of the test group (single dose of ACX017 (SEQ ID NO:1) and placebo group over the course of eight hours.
Figure 4:
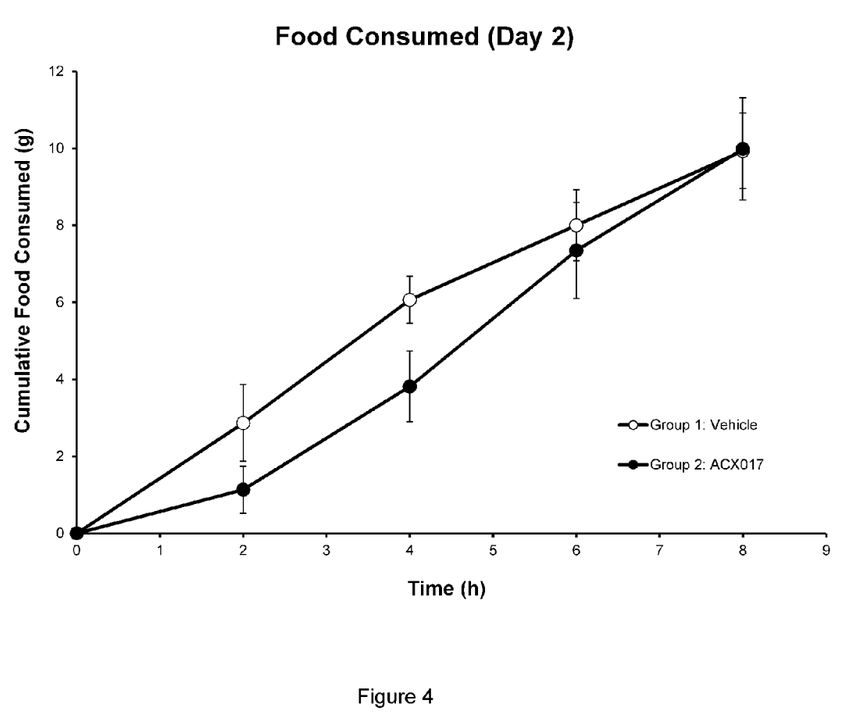
Figure 5:
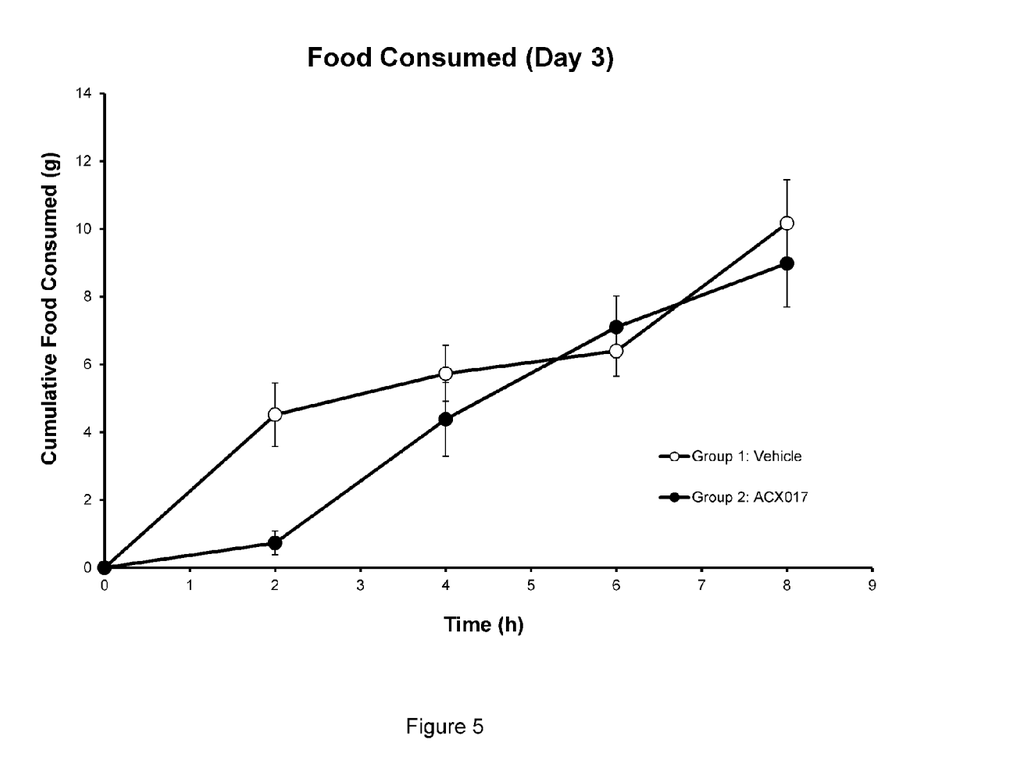
Figure 6:
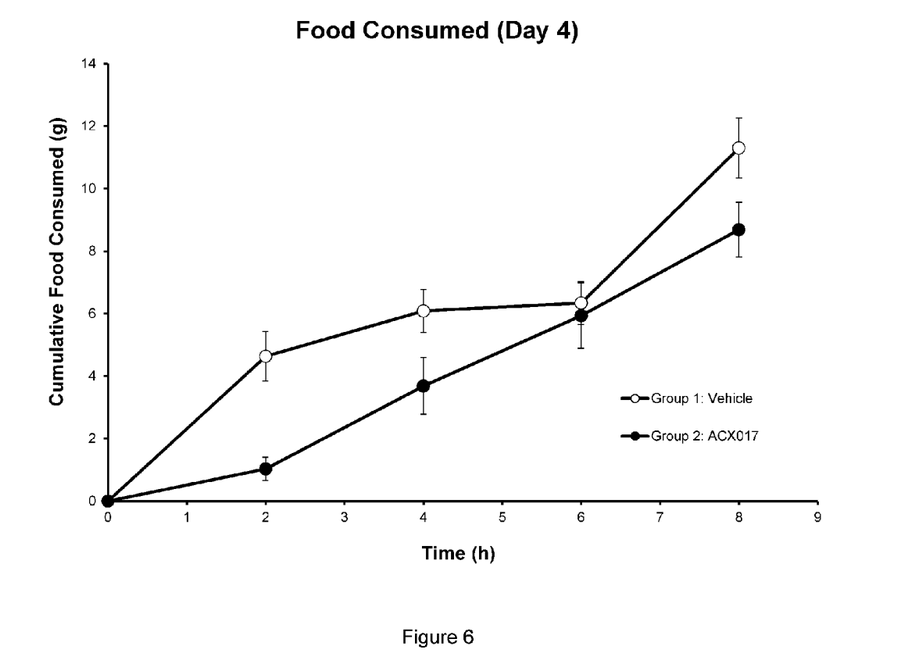

Results. As seen in FIG. 1, ACX017 demonstrated agonist activity against the CGRP receptor with an approximate EC50 concentration of 105 nM. In contrast, FIG. 2 shows that ACX017 did not activate the adrenomedullin 2 (AM2) receptor. As such ACX017 was shown to exhibit binding and functional specificity to the CGRP receptor in a dose dependent response.

Example 2

Food Intake Study. The effect of a CGRP agonist, in accordance with the present invention, on food intake over time both within and across several days of treatment was evaluated. Study was performed by Explora BioLabs, San Diego, Calif. and animals treated in accordance with its IACUC standards.

Sprague Dawley Rats, male, 400 g body weight (~12-14 wks old) were acclimated for at least seven days to housing environment and a 12 hour light/dark reverse cycle (light overnight/dark during the day. Animals were purpose-bred, specific pathogen-free, and experimentally naïve at the start of the study. Animals had ad libitum access to special Rodent Diet with 60% kcal % fat (D12492, Research Diets, New Brunswick, N.J.) and acidified water (pH 2.5-3.0) from arrival throughout the end of the study. Body weight at study initiation was at least 450 g. Animals that had: 1) significantly low body weight, 2) severe dehydration, or 3) wounds from fighting were excluded from the study.

On Day 0, 12 animals were randomized into two groups, Test and Control, to obtain similar body weight averages between groups. Animals were dosed via a single intraperitoneal injection, with either ACX017 (SEQ. ID NO:1) (Test group) or vehicle (Control group) each day, for four days. On each day, dosing was performed in the hour prior to the end of the light phase. ACX017 was dosed at 150 µg/kg in a 10% DMSO aqueous solution. Both ACX017 and vehicle were delivered as 1 mL/kg doses.

Food consumption was measured pre-dose and at 2, 4, 6 and 8 hours post dose. Food intake was measured by weighing food hoppers on Days 1, 2, 3 and four in the hour before end of the light phase and at 2, 4, 6 and 8 hours post dosing.

Average food intake for each of the Test and Control groups at each time point post dosing was determined. Cumulative food intake for each group over the entire test period (8 hours) is provided in graph form in FIGS. 1-4 for each of Days 1-4, respectively.

Consistently, ACX017 suppressed appetite in the Test group for at least about four hours after dosing as evidenced by reduced food intake during that period compared to the Control group at four hours. As such ACX017 (SEQ ID NO: 1) can cause appetite suppression in a subject, as demonstrated.

All documents cited herein are hereby incorporated by reference in their entirety.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone. A and B together, A and C together, B and C together, and/or A, B, and C together, etc). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

---

SEQUENCE LISTING

```
<160> NUMBER OF SEQ ID NOS: 10

<210> SEQ ID NO 1
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 1

Ala Cys Asp Thr Ala Thr Cys Val Leu Gly Arg Leu Ser Gln Glu Leu
 1               5                  10                  15

His Arg Leu Gln Thr Tyr Pro Arg Thr Asn Val Gly Ser Lys Ala Phe
            20                  25                  30

<210> SEQ ID NO 2
```

```
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 2

Ala Cys Asp Thr Ala Thr Cys Val Leu Gly Arg Leu Ser Gln Glu Leu
 1               5                  10                  15

His Arg Leu Gln Thr Tyr Pro Thr Asn Val Gly Ser Lys Ala Phe
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 3

Cys Asp Thr Ala Thr Cys Val Leu Gly Arg Leu Ser Gln Glu Leu His
 1               5                  10                  15

Arg Leu Gln Thr Tyr Pro Arg Thr Asn Val Gly Ser Lys Ala Phe
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 4

Cys Asp Thr Ala Thr Cys Val Leu Gly Arg Leu Ser Gln Glu Leu His
 1               5                  10                  15

Arg Leu Gln Thr Tyr Pro Thr Asn Val Gly Ser Lys Ala Phe
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 5

Ala Cys Asp Thr Ala Thr Cys Met Leu Gly Arg Tyr Thr Gln Asp Phe
 1               5                  10                  15

Asn Arg Phe His Thr Phe Pro Arg Thr Asn Val Gly Ser Lys Ala Phe
            20                  25                  30

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Ala or Cys or is not present
<220> FEATURE:
<221> NAME/KEY: VARIANT
<222> LOCATION: 2
<223> OTHER INFORMATION: Xaa = Cys, Ser or Gly, provided that at least
      one of X1 and X2 is Cys and only one of X1 or X2 is Cys
<220> FEATURE:
```

```
<221> NAME/KEY: VARIANT
<222> LOCATION: 3
<223> OTHER INFORMATION: Xaa = Asp or Asn
<220> FEATURE:
<221> NAME/KEY: VARIANT
<222> LOCATION: 5
<223> OTHER INFORMATION: Xaa = Ala or Ser and wherein the terminal Cys
      of X1 is capable of forming a disulfide bridge with the Cys
      residue in X1 or X2

<400> SEQUENCE: 6

Xaa Xaa Xaa Thr Xaa Thr Cys
 1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)...(1)
<223> OTHER INFORMATION: Xaa = Val or Met
<220> FEATURE:
<221> NAME/KEY: VARIANT
<222> LOCATION: (5)...(5)
<223> OTHER INFORMATION: Xaa = Leu or Tyr
<220> FEATURE:
<221> NAME/KEY: VARIANT
<222> LOCATION: (6)...(6)
<223> OTHER INFORMATION: Xaa = Ser or Thr
<220> FEATURE:
<221> NAME/KEY: VARIANT
<222> LOCATION: (8)...(8)
<223> OTHER INFORMATION: Xaa = Asp or Glu
<220> FEATURE:
<221> NAME/KEY: VARIANT
<222> LOCATION: 9, 12
<223> OTHER INFORMATION: Xaa = Phe or Leu
<220> FEATURE:
<221> NAME/KEY: VARIANT
<222> LOCATION: (10)...(10)
<223> OTHER INFORMATION: Xaa = His or Asn
<220> FEATURE:
<221> NAME/KEY: VARIANT
<222> LOCATION: (13)...(13)
<223> OTHER INFORMATION: Xaa = His or Gln
<220> FEATURE:
<221> NAME/KEY: VARIANT
<222> LOCATION: (15)...(15)
<223> OTHER INFORMATION: Xaa = Phe or Tyr

<400> SEQUENCE: 7

Xaa Leu Gly Arg Xaa Xaa Gln Xaa Xaa Xaa Arg Xaa Xaa Thr Xaa
 1               5                  10                  15

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Arg or Gln
<220> FEATURE:
<221> NAME/KEY: VARIANT
<222> LOCATION: 4
<223> OTHER INFORMATION: Xaa = Asn or Ala

<400> SEQUENCE: 8

Pro Xaa Thr Xaa Val Gly Ser Lys Ala Phe
```

```
<210> SEQ ID NO 9
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Ala Cys Asp Thr Ala Thr Cys
 1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 10

Pro Arg Thr Asn Val Gly Ser Lys Ala Phe
 1               5                  10
```

What is claimed is:

1. A calcitonin gene-related peptide (CGRP) agonist having the structure of Formula I:

$$X^1\text{—}Y^1\text{—}Z^1 \quad (I)$$

wherein:

$X^1$ is an N-terminal fragment comprising six or seven amino acid residues having the general formula:

$$X_1\ X_2\ X_3\ Thr\ X_4\ Thr\ Cys \quad (SEQ\ ID\ NO:\ 6)$$

wherein $X_1$ is Ala or Cys or is not present, $X_2$ is Cys, Ser or Gly, provided however that at least one of $X_1$ and $X_2$ is Cys and only one of $X_1$ or $X_2$ is Cys, $X_3$ is Asp or Asn and $X_4$ is Ala or Ser and wherein the terminal Cys of $X^1$ is capable of forming a disulfide bridge with the Cys residue in $X_1$ or $X_2$;

$Y^1$ is a central core comprising 15 amino acid residues, said central core having the general formula:

$$X_5\ Leu\ Gly\ Arg\ X_6\ X_7\ Gln\ X_8\ X_9\ X_{10}\ Arg\ X_{11}\ X_{12}\ Thr\ X_{13} \quad (SEQ\ ID\ NO:\ 7)$$

wherein $X_5$ is Val or Met, $X_6$ is Leu or Tyr, $X_7$ is Ser or Thr, $X_8$ is Asp or Glu, $X_9$ is Phe or Leu, $X_{10}$ is His or Asn, $X_{11}$ is Phe or Leu, $X_{12}$ is His or Gln, $X_{13}$ is Phe or Tyr; and $Z^1$ is a C-terminal fragment comprising ten amino acid residues, said C-terminal fragment comprising a C-terminal amide, said fragment having the general formula:

$$Pro\ X_{14}\ Thr\ X_{15}\ Val\ Gly\ Ser\ Lys\ Ala\ Phe \quad (SEQ\ ID\ NO:\ 8),$$

wherein $X_{14}$ is Arg or Gln and $X_{15}$ is Asn or Ala; or pharmaceutically acceptable salt thereof.

2. The calcitonin gene-related peptide (CGRP) agonist according to 1, wherein $X_1$ is Cys, and $X_2$ is Ser or Gly.

3. The calcitonin gene-related peptide (CGRP) agonist according to 1, wherein $X_2$ is Cys, and $X_1$ is Ala.

4. The calcitonin gene-related peptide (CGRP) agonist according to claim 1, wherein $X^1$ comprises SEQ ID NO: 9.

5. The calcitonin gene-related peptide (CGRP) agonist according to claim 1, wherein $Z^1$ comprises SEQ ID NO: 10.

6. A calcitonin gene-related peptide (CGRP) agonist selected from the group consisting of SEQ ID NO:1, SEQ ID NO:2, SEQ ID NO:3, SEQ ID NO:4 and SEQ ID NO:5 or a pharmaceutically acceptable salt thereof.

7. The calcitonin gene-related peptide (CGRP) agonist of claim 1, wherein the amide group is —C(O)NH$_2$.

8. A pharmaceutical composition comprising:
a pharmaceutically acceptable excipient; and
the calcitonin gene-related peptide (CGRP) agonist of claim 1.

9. A method of treating a metabolic disorder comprising administering to a subject in need thereof an effective amount of the calcitonin gene-related peptide (CGRP) agonist according to claim 1.

10. The method of claim 9, wherein the metabolic disorder is selected from the group comprising diabetes and obesity.

11. The method of claim 10, wherein the subject is human.

12. A pharmaceutical composition comprising:
a pharmaceutically acceptable excipient; and
the calcitonin gene-related peptide (CGRP) agonist of claim 6.

13. A method of treating a metabolic disorder comprising administering to a subject in need thereof an effective amount of the calcitonin gene-related peptide (CGRP) agonist according to claim 6.

\* \* \* \* \*

UNITED STATES PATENT AND TRADEMARK OFFICE
CERTIFICATE OF CORRECTION

PATENT NO. : 9,951,115 B2
APPLICATION NO. : 14/908515
DATED : April 24, 2018
INVENTOR(S) : Christopher Joseph Soares It is certified that error appears in the above-identified patent and that said Letters Patent is hereby corrected as shown below:

In the Specification

In Column 1 at Line 20, Change "CSOAR.002W0" to --CSOAR.002WO--.

In Column 1 at Line 44-45, Change "Pharmacol," to --Pharmacol.--.

In Column 1 at Line 49, Change "see," to --(see,--.

In Column 1 at Line 51, Change "279(8):7264-7274)," to --279(8):7264-7274).--.

In Column 2 at Line 5, Change "Pharmacol, Sci," to --Pharmacol. Sci.--.

In Column 2 at Line 12, Change "CGRP-1" to --CGRP-I--.

In Column 2 at Line 12, Change "CGRP-11," to --CGRP-II,--.

In Column 3 at Line 29, After "$X_5$" delete "Lys".

In Column 6 at Line 57 (approx.), Change "entirely." to --entirety.--.

In Column 7 at Line 8, Change "Generality," to --Generally,--.

In Column 7 at Line 34, Change "sueeinate," to --succinate,--.

In Column 8 at Line 21 (approx.), Change "(1Ie)" to --(Ile)--.

In Column 8 at Line 28 (approx.), Change "1;" to --I;--.

In Column 9 at Line 29, Change "CORP" to --CGRP--.

Signed and Sealed this
Sixteenth Day of July, 2019

Andrei Iancu
*Director of the United States Patent and Trademark Office*

CERTIFICATE OF CORRECTION (continued)
U.S. Pat. No. 9,951,115 B2

In Column 10 at Line 4, Change "No, WO 93/25221," to --No. WO 93/25221,--.

In Column 10 at Line 11 (approx.), Change "transmucosai" to --transmucosal--.

In Column 10 at Line 24, After "conventional" insert --mixing,--.

In Column 12 at Line 19, Change "8 µl" to --8 µL--.

In Column 12 at Line 31, Change "against" to --agonist--.

In Column 14 at Line 34, Change "etc)." to --etc.).--.

In the Claims

In Column 19 at Line 49 (approx.), In Claim 1, change "Gin," to --Gln,--.

In Column 19 at Line 59 (approx.), In Claim 2, after "to" insert --claim--.

In Column 20 at Line 28, In Claim 3, after "to" insert --claim--.